United States Patent [19]
Jennings et al.

[11] Patent Number: 6,001,989
[45] Date of Patent: Dec. 14, 1999

[54] NUCLEOTIDE BASED ENDONUCLEASES

[75] Inventors: Philip Anthony Jennings, Chatswood West; Maxine June Mc Call, Gladesville; Philip Hendry, Rozelle, all of Australia

[73] Assignee: Gene Shears Pty Limited, Canberra, Australia

[21] Appl. No.: 08/218,656

[22] Filed: Mar. 28, 1994

Related U.S. Application Data

[63] Continuation of application No. 07/717,602, Jun. 19, 1991, Pat. No. 5,298,612.

[30] Foreign Application Priority Data

Jun. 19, 1990 [AU] Australia .............................. PK0679/90
Dec. 21, 1990 [AU] Australia .............................. PK4002/90

[51] Int. Cl.$^6$ .............................. C07H 21/04; C12Q 1/68
[52] U.S. Cl. ...................... 536/24.5; 536/23.1; 536/23.2; 435/6; 435/91.31; 435/375
[58] Field of Search ....................... 435/6, 91.31, 172.3, 435/240.2, 320.1; 536/23.1, 23.2, 24.5; 514/44

[56] References Cited

U.S. PATENT DOCUMENTS

| | | | |
|---|---|---|---|
| 4,511,713 | 4/1985 | Miller et al. ................................. | 435/6 |
| 4,987,071 | 1/1991 | Cech ..................................... | 536/23.2 |
| 5,023,243 | 6/1991 | Tullis et al. ............................. | 514/44 |
| 5,149,796 | 9/1992 | Rossi ..................................... | 514/44 |

FOREIGN PATENT DOCUMENTS

| | | |
|---|---|---|
| 5130190 | 11/1990 | Australia . |
| 6218690 | 3/1991 | Australia . |
| 8905852 | 6/1989 | WIPO . |

OTHER PUBLICATIONS

Boehm, S., (1987) FEBS Letter 220:283–287.
Bruening, G. (1989) Methods of Enzym. 180:546–558.
Cech, T.R. (1987) Science 236:1532–1539.
Chuat, J. et al. (1989) Biochem & Biophys Res Comm. 162:1025–1029.
Forster, A.C. and Symons, R.H. (1987) Cell 49:211–220.
Cotten, M., et al. (1989) The EMBO Journal 8:3861–3866.
Dahm, S.C., et al. (1990) Biochimie 72:819–823.
Eckner, R. et al., (1991) The EMBO Journ. 10:3513–3522.
Forster, A.C. et al. (1988) NAture 334:265–267.
Goodchild, J., et al. (1991) Archives to Biochem & Biophys. 284(2):386–391.
Goodchild, J. et al. (1990) Poster No. 12 at Conf in San Diego.
Haseloff, et al. (1988) Nature 334:585–591.
Huillier, A. et al. Abstract from Conf. proceedings.
Hutchins, C.J. et al. (1986) Nucleic Acids Research 14:3627–3635.
Haseloff et al. (1989) Gene 82:43–52.
Jefferies, A.C., et al. (1989) Nucl. Acids Res. 17:1371–1377.
Forster et al. (1987) Cell 50:9–16.
Kikuchi, Y. et al., (1991) Nucleic Acids Res. 19:6715–6755.
Koizumi, et al., (1988) FEBS Letters 228:228–230.
Koizumi, et al. (1989) Nucleic Acids Res. 17:7059–7071.
Lamb, J.W., et al. (1990) J. Gen. Virol. 71:2257–2264.
McClain et al. (1987) Science 238:527–530.
Miller et al. (1991) Virology 183:711–720.
Perreault, J–P, et al. (1991) Biochem. 30:4020–4025.
Ruffner, D.E. et al. (1989) Gene 82:31–41.
Ruffner, D.E. et al. (1990) Biochemistry 29:10695–10702.
Sampson et al. (1987) Cold Spring Harbor Sym Quant Biol 52:267–275.
Sheldon et al. (1989) Nucl Acid Res. 17: 5679–5685.
Sarver, et al. (1990) Science 247:1222–1224.
Saxena, et al. (1990) J. Biol. Chem. 265:17106–17109.
Scanlon, K. et al. (1991) Proc. Natl. Acad. Sci. 88:10591–10595.
Uhlmann et al. (1990) Chem. Revs. 90:544–584.
Sheldon, C.C. et al. (1989) Nucleic Acids Res. 17:5665–5678.
Symons, R.H. (1989) Tibs, 14:445–450.
Tabler, M. et al. (1991) Gene 108:175–183.
Uhlenbeck, et al. (1987) Nature 328:596–600.
Yang, et al. (1990) Biochemistry 29:11156–11160.
Zaug, etal. (1986 A) Science, 231:473–474.
Zaug, et al. (1986 B) Nature 234:429–433.
Perreault et al. (1990) Nature 344:565–567; and.
Cameron et al. (1989) Proc. Natl. Acad. Sci. 86:9139–9143.
Barinaga, Science 262:1521–1514, 1993.
Johnston et al., Science 260:1286–1293.
Branch TIBS 23:45–50 Feb. 1998.

*Primary Examiner*—John L. LeGuyader
*Attorney, Agent, or Firm*—John P. White; Cooper & Dunham LLP

[57] ABSTRACT

This invention provides catalytic molecules capable of cleaving target nucleotide sequences. More specifically, the invention provides an endonuclease having nucleotide sequences which are of sufficient length to allow hybridisation to a target nucleotide sequence desired to be cleaved. The endonuclease contains a catalytic region comprising ribonucleotides and/or deoxyribonucleotides, or derivatives thereof which act to cleave a phosphodiester bond of the substrate nucleotide sequence. The catalytic region comprises nucleotides or derivatives thereof which are linked by linking groups which may comprise ribonucleotides, deoxyribonucleotides or combinations thereof.

The endonucleases of the invention are useful in the cleavage of target RNAs associated with disease in humans and animals and in the inactivation of RNA transcripts in eukaryotic and prokaryotic cells, as well as the cleavage of RNA transcripts in-vitro.

4 Claims, 2 Drawing Sheets

NUCLEOTIDE BASED ENDONUCLEASES

This application is a continuation of U.S. Ser. No. 07/717,602, filed Jun. 19, 1991, now U.S. Pat. No. 5,298,612, issued Mar. 29, 1994.

This invention generally relates to endonucleases which are capable of cleaving nucleic acids; vectors encoding endonucleases; host cells and organisms either modified by and/or containing or encoding nucleic acid endonucleases; and to methods for the cleavage and/or inactivation of nucleic acid molecules in-vivo or in-vitro.

FIELD OF THE INVENTION

There have previously been described catalytic endoribonucleases comprised of RNA which are capable of effecting the cleavage of target RNA. Such endoribonucleases generally fall into two categories. The first, are based on the mitochondrial intervening sequence (IVS) RNA of the organism tetrahymena, such as described by Zaug et al. (Nature, Vol. 324, 429–433, 1986). The second class of endoribonucleases are the result of pioneering work by Haseloff and Gerlach (Nature, Vol. 334, 585–591, 1988) on the self-cleaving regions of plant viral RNA.

This invention is directed to hitherto unknown endonucleases.

SUMMARY OF THE INVENTION

Figure 1A:
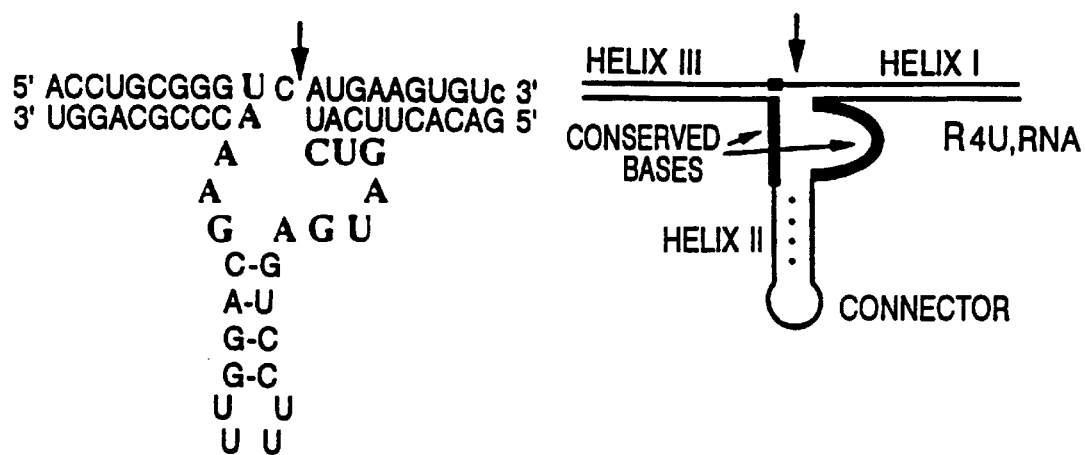
FIG. 1A–1B shows base sequences, schematic representations and the names of various endonucleases. Conserved ribonucleotides are depicted by bold type and thick lines. Other ribonucleotides are depicted by upper case letters and thin lines. Deoxyribonucleotides are depicted by lower case letters and wavy lines. The nomenclature for the endonucleases is as follows: R indicates a ribozyme containing helix II, M denotes the compound not containing helix II, and MS denotes the compound and substrate in the same molecule; the numbers and nucleotide designations indicate the bases in the connector, and the RNA or DNA refers to the nucleotides in the arms that form helices I and III with the substrate.
Figure 1B:
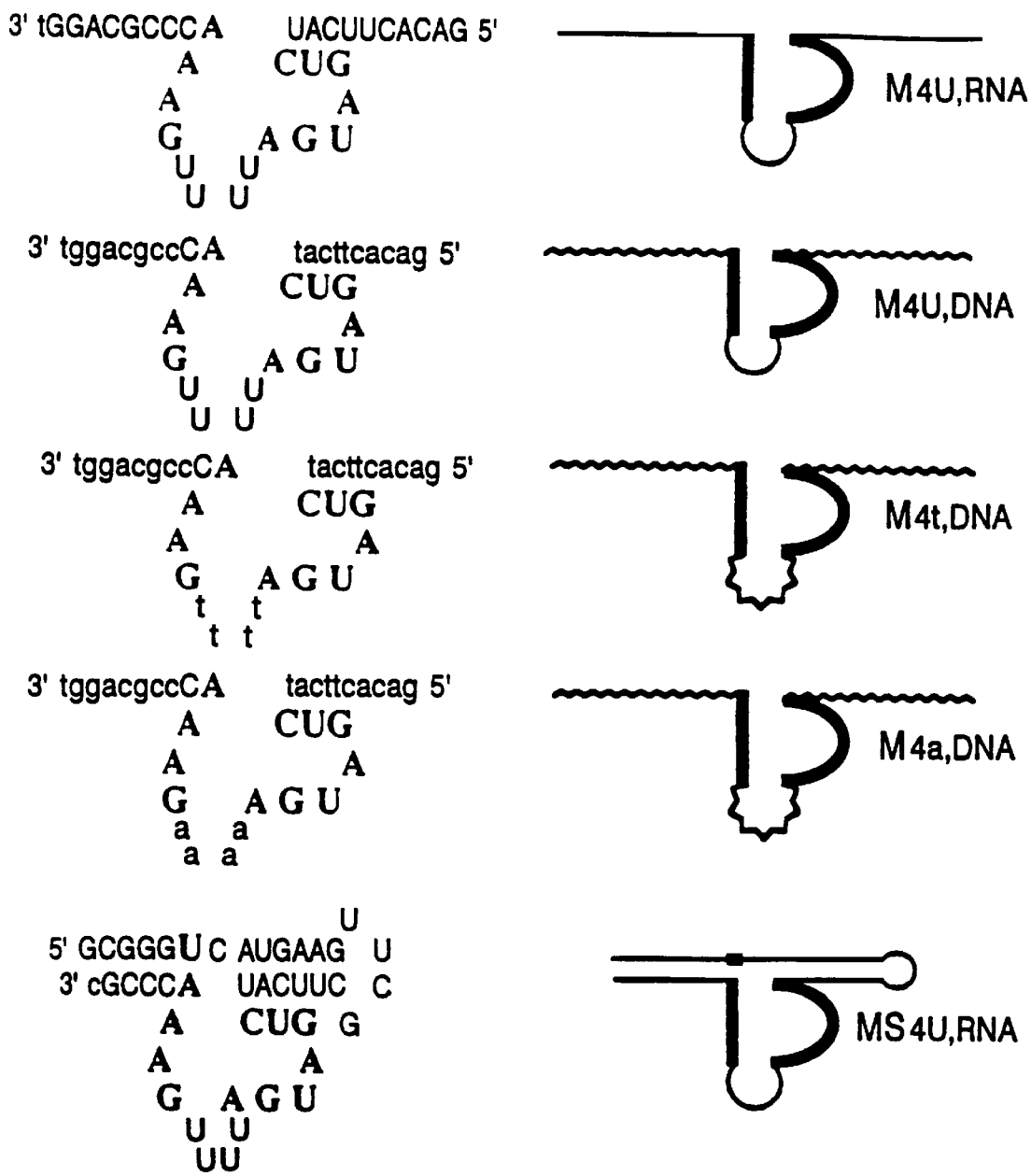

In accordance with a first aspect of this invention, there is provided an endonuclease of the formula (I)

wherein X and Y represent nucleotide sequences comprised of deoxyribonucleotides, ribonucleotides, or combinations thereof or derivatives thereof; said nucleotide sequences being of sufficient length to allow hybridization to a target nucleic acid sequence desired to be cleaved by said endonuclease;

and wherein M represents a catalytic region of the formula (II):

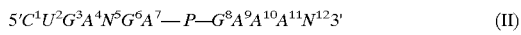

where, A, G, C and U respectively represent bases adenine, guanine, cytosine and uracil which may be in the form of deoxyribonucleotides, ribonucleotides, or combinations thereof or derivatives thereof; and $N^{12}$ is selected from any of the bases adenine, guanine, cytosine, uracil or thymine, or derivatives thereof;

and wherein;

P is one or more nucleotides, which nucleotides may be deoxyribonucleotides, ribonucleotides, or a combination of one or more deoxyribonucleotides and one or more ribonucleotides, or derivatives thereof, wherein if said nucleotides solely comprise ribonucleotides and the nucleotide sequences X and Y are solely comprised of ribonucleotides, then said ribonucleotides of the group P are not base paired to one another; or a bond or any atom or any group of interconnected atoms linking nucleotides $A^7$ and $G^8$, which does not destroy the cleavage capability of the catalytic region and which is not solely comprised of nucleotides.

For the sake of convenience, such endonucleases may be referred to as minizymes.

In the catalytic region M, nucleotide additions, deletions or replacements may be made with the proviso that endonuclease activity is not destroyed. For example, any one of nucleotides $C^1$ to $A^{11}$ may be substituted with one or more ribo- and/or deoxyribonucleotides containing bases such as adenine, guanine, cytosine, methyl cytosine, uracil, thymine, xanthine, hypoxanthine, inosine, or other methylated bases. Nucleotide bases and deoxynucleotide bases are well known in the art and are described, for example in Principles of Nucleic Acid Structure (Ed, Wolfram Sanger, Springer-Verlag, New York, 1984) which is incorporated herein in its entirety by reference. Nucleotides $C^1$ to $N^{12}$ may be substituted with any ribonucleotide or deoxyribonucleotide known per se, with the proviso that endonuclease activity, particularly endoribonuclease activity, is not lost. Endoribonuclease activity may be readily and routinely assessed as will be described hereinafter.

It is preferred that the catalytic region be comprised of ribonucleotides. Notwithstanding this, one or more of the nucleotides $C^1$ to $A^{11}$ of the catalytic region may be in the form of deoxyribonucleotides as long as endoribonuclease activity is not lost.

Ribonucleotide and deoxyribonucleotide derivatives or modifications are well known in the art, and are described, for example, in Principles of Nucleic Acid Structure (Supra, particularly pages 159–200), and in the CRC Handbook of Biochemistry (Second edition, Ed, H. Sober, 1970) which is incorporated herein by reference.

Nucleotides comprise a base, sugar and a monophosphate group. Accordingly, nucleotide derivatives or modifications may be made at the level of the base, sugar or monophosphate groupings.

A large number of modified bases are found in nature, and a wide range of modified bases have been synthetically produced (see Principles of Nucleic Acid Structure and CRC Handbook of Biochemistry, Supra). For example, amino groups and ring nitrogens may be alkylated, such as alkylation of ring nitrogen atoms or carbon atoms such as $N_1$ and $N_7$ of guanine and $C_5$ of cytosine; substitution of keto by thioketo groups; saturation of carbon=carbon double bonds, and introduction of a C-glycosyl link in pseudouridine. Examples of thioketo derivatives are 6-mercaptopurine and 6-mercaptoguanine.

Bases may be substituted with various groups, such as halogen, hydroxy, amine, alkyl, azido, nitro, phenyl and the like.

The sugar moiety of the nucleotide may be modified according to well known methods in the art (see Principles of Nucleic Acid Structure and CRC Handbook of Biochemistry, Supra). This invention embraces various modifications to the sugar moiety of nucleotides as long as such modifications do not abolish cleavage activity of the endonuclease. Examples of modified sugars include replacement of secondary hydroxyl groups with halogen, amino or azido groups; 2'-methylation; conformational variants such as the 02'-hydroxyl being cis-oriented to the glycosyl $C_1$-N link to provide arabinonucleosides, and conformational isomers at carbon $C_1$, to give α-nucleosides, and the like.

The phosphate moiety of nucleosides is also subject to derivatisation or modifications, which are well known in the art. For example, replacement of oxygen with nitrogen, sulphur or carbon derivatives to respectively give phosphoramidates, phosphorothioates and phosphonates. Substitutions of oxygen with nitrogen, sulphur or carbon derivatives may be made in bridging or non bridging positions. It has been well established from work involving antisense oligonucleotides that phosphodiester and phosphorothioate derivatives may efficiently enter cells (particularly when of short length), possibly due to association with a cellular receptor. Methylphosphonates are probably readily taken up by cells by virtue of their electrical neutrality.

Deoxyribonucleotide or ribonucleotide derivatives as referred to in this specification embody one or more of the modifications referred to above which do not destroy the cleavage capability of the endonuclease.

Bases and/or nucleotides 1 to 11 of the catalytic region may be substituted with other chemical species, such as an amino-acid side chain or linkers which may or may not incorporate other chemical entities, e.g. acidic or basic groups. For example, $G^3$ may be substituted with tyrosine, and $C^1$ or $A^{11}$ similarly substituted with histidine. In some instances it may prove possible to delete a functionally important chemical species (e.g., nucleotide or amino-acid side chain) and provide this as part of the substrate or as a co-factor which transactivates the endonuclease. Such derivatives which possess endonuclease activity are within the scope of the present invention.

Endonuclease activity is readily, simply and routinely tested by incubating the endonuclease with its substrate and thereafter assessing whether cleavage of the substrate takes place. For example, cleavage of a target mRNA takes place after the trinucleotide sequence X'UY' where X' and Y' represent any ribonucleotide, and which may be the same or different and U represents a ribonucleotide having the base uridine. Preferred cleavage sites include GUC, GUU, GUA and UUC. By way of example, suitable reaction conditions may comprise a temperature from about 4° C. to about 60° C. (preferably about 20 to 55° C.), pH from about 7.0 to about 9.0 and salt (such as $Mg^{2+}$) from about 1 to about 100 mM (preferably 1 to 20 mM). Endonucleases containing a small number of nucleotides in each of the groups X and Y of formula (I) (such as four nucleotides) in each of groups X and Y would generally be incubated at lower temperatures, such as about 20° C. to about 25° C. to aid duplexing of complementary nucleotide sequences in the endonuclease sequences X and Y and the substrate. The endonuclease would generally be in an equimolar ratio to the substrate or in excess thereof. However, as the endonuclease may act as an enzyme, cleaving substrate without consumption, the ratio of endonuclease to substrate is not of importance.

A target RNA containing a suitable cleavage site as mentioned above, such as GUC site may be incubated with an endonuclease which, for example, may contain one or more modifications within the catalytic region. The nucleotide sequences X and Y of the formula (I) are selected so as to be complementary (that is, capable of forming base pairs) to nucleotide sequences flanking the cleavage site in the target RNA. On incubation of the endonuclease and its substrate an enzyme/substrate complex is formed, as a result of base pairing between complementary nucleotides in the endonuclease and the substrate. Nucleotide sequences X and Y of the formula (I) and nucleotide sequences flanking the cleavage site in the substrate form a double stranded duplex as a result of base pairing, which base pairing is well known in the art (Sambrook, J. et al., Molecular Cloning, A Laboratory Manual, 2nd Edition, Cold Spring Harbor Press, 1989, which is incorporated herein by reference). The formation of a double stranded duplex between complementary nucleotides may be referred to as hybridization (Sambrook, et al., Supra). Hybridization or duplex formation between the endonuclease and its substrate can be readily assessed, for example, by labelling one or both components, such as with a radiolabel, and then subjecting the reaction mixture to polyacrylamide gel electrophoresis under non-denaturing conditions (Sambrook et al., Supra). If the target is cleaved on incubation with the endonuclease it is active and is within the scope of this invention. Accordingly, an endonuclease containing a nucleotide derivative may be simply tested for endonuclease activity in a routine manner.

As will be readily appreciated by workers in the field to which this invention relates, the cleavage of a target RNA may be readily assessed by various methods well known in the art (for example, see Sambrook et al., Supra). Cleavage may, for example, be assessed by running the reaction products (where the substrate is radioactively labelled) on acrylamide, agarose, or other gel systems, and then subjecting the gel to autoradiography or other analytical technique to detect cleavage fragments (Sambrook et al., Supra).

Where the group P represents a bond it may represent a chemical bond or atom or group of interconnected atoms between nucleotides $A^7$ and $G^8$. The bond between nucleotides is between the base or sugar moiety, i.e., sugar to sugar, base to sugar, or base to base. Inter base crosslinking is described, for example, by Petric et al. (1991), Nucleic Acid. Res., 19: 585, which is incorporated herein by reference. The bond may extend from any position on the base or sugar ring or from any functional group on the base or sugar ring, again with the proviso that the endonuclease is capable of substrate cleavage.

The group P of the formula (II) may represent one or more nucleotides, which nucleotides may be deoxyribonucleotides, ribonucleotides, or a combination of one or more deoxyribonucleotides or one or more ribonucleotides, or derivatives thereof, wherein said derivatives are as described herein. Where P comprises a nucleotide sequence, the nucleotide sequence may comprise a ribonucleotide sequence or a combination of one or more ribonucleotides and one or more deoxyribonucleotides, in which none of these bases are paired, or at least one of the bases is base paired (i.e., this including where all of the bases are base paired, and where not all of the bases are paired). Alternatively, the group P may comprise a deoxyribonucleotide sequence in which none of the bases are paired or at least one of the bases are paired (again this including where all of the bases are base paired, and where not all of the bases are base paired). Where the nucleotide sequences X and Y are comprised solely of ribonucleotides, and the group P is comprised solely of ribonucleotides, the ribonucleotides of the group P are not base paired to one another. Optionally, where nucleotide sequences X and Y are comprised solely of deoxyribonucleotides, and the group P is comprised solely of deoxyribonucleotides, the deoxyribonucleotides of the group P may not be base paired.

Applicants have found that base pairing in the group P is not required for cleavage of a target RNA. Accordingly, when nucleotide sequences X and Y are comprised solely of ribonucleotides and the group P is comprised solely of ribonucleotides, the ribonucleotides of the group P may be base paired for purposes other than to effect cleavage of a target RNA. Such purposes would include to allow the binding of cellular factors, such as RNA binding proteins or other cellular factors. Similarly, where the nucleotide sequences X and Y are comprised solely of deoxyribonucleotides, and the group P is comprised solely of deoxyribonucleotides, the deoxyribonucleotides of the group P may be base paired for purposes other than involvement in endonuclease cleavage, such as interaction with DNA binding proteins and other cellular factors, which may, for example, effect cellular distribution of the endonuclease.

Where deoxyribonucleotides, ribonucleotides, combinations thereof, and derivatives thereof, are said to be not base paired, a person of ordinary skill in the art will understand this to mean that the nucleotides are not base paired to one another according to known nucleotide base pairing, namely Watson-Crick base pairs and Hoogsteen base pairs, and the like (Principles of Nucleic Acid Structure, Supra).

The absence of base pairing is an advantageous feature of this invention as endonucleases comprising a minimal number of nucleotides may be produced according to standard methods hereinafter described. The applicants have surprisingly discovered that base pairs between nucleotides in the group P are not required to permit the endonuclease of this invention to cleave its target substrate. Accordingly, the group P may comprise any number of non base paired nucleotides, for example, two nucleotides (such as TT), four nucleotides (such as AAAA, UUUU, TTTT, etc.) or five nucleotides (such as TTTTT). The nucleotide sequence of the group P under these circumstances is not of importance and the number of nucleotides is also not of importance. Generally speaking, the group P may comprise from 1 to 20 non base paired nucleotides and more preferably may contain from 2 to 6 non base paired nucleotides. The main consideration to take into account is that the resultant endonuclease is capable of substrate cleavage. This can be readily measured without undue experimentation in standard cleavage assays on an appropriate target nucleotide sequences as hereinbefore described.

The group P in formula (II) may comprise ribonucleotides, deoxyribonucleotides, or at least one deoxyribonucleotide and at least one ribonucleotide, or derivatives thereof wherein all nucleotides are base paired, or not all of the nucleotides are base paired, as previously described. Complementary nucleotides in the nucleotide sequence P linking nucleotides $A^7$ and $G^8$ of the formula (II), may be base paired by Watson-Crick base pairs, Hoogsteen base pairs, or other base pairing known in the art. Where the nucleotide sequence of the group P is partly base paired (that is, not all nucleotides are base paired), there may be provided regions of base pairing and one or more single-stranded regions, for example, a base paired stem and a loop of non base paired nucleotides. For example, a stem and loop arrangement is described by Haseloff and Gerlach (Supra), and has the following sequence:

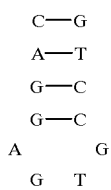

A sequence forming such a stem/loop structure may, in accordance with this invention, be comprised of deoxyribonucleotides, ribonucleotides, or a combination of deoxyribonucleotides and ribonucleotides.

Notwithstanding the above, it is preferred that the nucleotides of the group P are not base paired. The absence of a base paired structure may reduce steric interference of the endonuclease with its substrate or other nucleic acid sequences (thus increasing endonuclease activity), and may reduce the likelihood of non-favourable base pairing interactions.

The group P of the formula (II) may comprise a nucleotide sequence as herein described wherein one or more ribonucleotides and/or deoxyribonucleotides are replaced with a linker which connects adjacent nucleotides. Any chemical linker, that is any group of interconnected atoms, may be used to link nucleotides $A^7$ and $G^8$, or any one of nucleotides $C^1$ to $A^7$ with any one of nucleotides $G^8$ to $A^{10}$ wherein the endonuclease is capable of substrate cleavage. Examples of such linkers are described by Petric et al., Supra). Substrate cleavage may be readily assessed by simply incubating an endonuclease with its substrate as described hereinbefore.

One or more ribonucleotides and/or deoxyribonucleotides of the group P may be replaced, for example, with a linker selected from optionally substitited polyphosphodiester (such as poly(1-phospho- 3-propanol)), optionally substituted alkyl, optionally substituted polyamide, optionally substituted glycol, and the like. Optional substituents are well known in the art, and include alkoxy (such as methoxy, ethoxy and propoxy), straight or branch chain lower alkyl (such as $C_1$–$C_5$ alkyl), amine, aminoalkyl such as amino $C_1$–$C_5$ alkyl), halogen (such as F, Cl and Br) and the like. The nature of optional substituents is not of importance, as long as the resultant endonuclease is capable of substrate cleavage.

Additionally, suitable linkers may comprise polycyclic molecules, such as those containing phenyl or cyclohexyl rings. Such compounds would generally comprise suitable functional groups to allow coupling through reactive groups on nucleotides.

The nucleotides of the groups X and Y may be of any length and sequence sufficient to enable hybridization formation with complementary nucleotides in the target RNA, as described herein. The nucleotides may be in the form of deoxyribo- nucleotides, ribonucleotides, deoxyribonucleotide ribonucleotide hybrids, or derivatives thereof as hereinbefore described. These flanking sequences may be chosen to optimize stability of the endonuclease from degradation. For example, deoxyribonucleotides are resistant to the action of ribonucleases. Modified bases, sugars or phosphate linkages of nucleotides, such as phosphoramidate, or phgosphorothioate linkages in the phosphate backbone of the nucleotide sequences, may also provide resistance to nuclease attack. Binding affinity may also be optimised in particular circumstances, by providing nucleotides solely in the form of ribonucleotides, deoxyribonucleotides, or combinations thereof. In some circumstances it may be necessary to optimise the composition of the groups X and Y, to maximize target RNA cleavage. The cleavage activity of endonucleases having flanking nucleotide sequences which hybridise to target sequences and which are comprised wholly of deoxyribonucleotides may, in some circumstances, have reduced activity. In such circumstances optimisation may involve providing a mixture of deoxyribonucleotides and ribonucleotides in the nucleotide sequences X and Y. For example, nucleotides in the endonuclease which are proximal to the cleavage site in a target RNA may be in the form of ribonucleotides. The nucleotides $A^{11}$ and $N^{12}$ of the formula (II) interact with the target sequence adjacent to the cleavage site, with $A^{11}$ interacting with the U of the target sequence X'UY', where X' and Y' are as herein defined. The nucleotide $N^{12}$ is selected to be complementary to the nucleotide represented by X'. These nucleotides, or nucleotides in a 5' direction may, for example, be in the form of ribonucleotides. Where a target sequence is shown to be relatively resistant to certain embodiments of endonucleases of this invention, it may be necessary to provide nucleotide sequences X and Y partly or wholly in the form of ribonucleotides. Where desired, protection from nuclease attack as will be hereinafter described.

The respective 5' and 3' termini of the groups X and Y may be modified to stabilise the endonuclease from degradation. For example, blocking groups may be added to prevent terminal nuclease attack, in particular 3'–5' progressive exonuclease activity. By way of example, blocking groups may be selected from optionally substituted alkyl, optionally substituted phenyl, optionally substituted alkanoyl. Optional substituents may be selected from $C_1$–$C_5$ alkyl; halogen such as F, Cl or Br; hydroxy; amino; $C_1$–$C_5$ alkoxy and the like. Alternatively, nucleotide analogues such as phosphothioates, methylphosphonates or phosphoramidates or nucleoside derivatives (such as α-anomers of the ribose moiety) which are resistant to nuclease attack may be employed as terminal blocking groups.

Alternatively, groups which alter the susceptibility of the endonuclease molecule to other nucleases may be inserted into the 3' and/or 5' end of the endonuclease. For example, 9-amino-acridine attached to the endonuclease may act as a terminal blocking group to generate resistance to nuclease attack on the endonuclease molecules and/or as an intercalating agent to aid endonucleolytic activity. It will be readily appreciated that a variety of other chemical groups, e.g. spermine or spermidine could be used in a related manner.

Endonucleases of this invention may be covalently or non-covalently associated with affinity agents such as proteins, steroids, hormones, lipids, nucleic acid sequences, intercalating molecules (such as acridine derivatives, for example 9-amino acridine) or the like to modify binding affinity for a substrate nucleotide sequence or increase affinity for target cells, or localisation in cellular compartments or the like. For example, the endonucleases of the present invention may be associated with RNA binding peptides or proteins which may assist in bringing the endonuclease into juxtaposition with a target nucleic acid such that hybridization and cleavage of the target sequence may take place. Nucleotide sequences may be added to the 5' and 3' ends of the groups X and Y to increase affinity for substrates. Such additional nucleotide sequences may form triple helices with target sequences (Strobel, S. A., et al., (1991) Nature 350: 172–174 and references therein which are incorporated by reference) which may enable interaction with intramolecularly folded substrate. Alternatively, modified bases (non-natural or modified bases as described in Principles of Nucleic Acid Structure, Supra) bases within the additional nucleotide sequences may be used that will associate with either single stranded or duplex DNA generating base pair, triplet, or quadruplet, interactions with nucleotides in the substrate. Suitable bases would include inosine, 5'-methylcytosine, 5'-bromouracil and other such bases as are well known in the art, as described, for example, in Principles of Nucleic Acid Structure, Supra.

In accordance with another aspect of this invention there is provided an endonuclease of the formula (I) as hereinbefore described wherein one of said nucleotide sequences X or Y includes the target polynucleotide which is cleaved by the endonuclease. Such an embodiment may cause the release of active RNA fragments on cleavage of a target RNA, which fragments may themselves possess endonuclease activity.

In accordance with another aspect of this invention, there is provided a poly-endonuclease of the formula (IV):

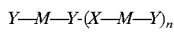

where

X, Y and M are as previously defined, and n is an integer of from 1 to 100.

Poly-endonucleases have the potential to act as anti-sense molecules (Helene, C. and J-J Toulmé (1990) Biochemica, Biophysica, Acta 1049: 99–125) as well as endonucleases. By "antisense" is meant the formation of a duplex or double stranded sequence as a result of base pairing between complementary bases of a target sequence and an antisense oligonucleotide, which prevents translation of said sequence as a result of duplex formation or the creation of a template for cleavage of the RNA by RNase H, a cellular ribonuclease which acts to cleave the RNA component of hybridised RNA and DNA sequences. The possibility of acting as antisense may also arise when the groups X and Y of the endonuclease of this invention contain a significant number of nucleotides, such as 30 or more nucleotides. A duplex formed between such an endonuclease and a target sequence may not dissociate or readily melt under ambient conditions.

In accordance with yet another aspect of this invention, there is provided a composition comprising an effective amount of an endonuclease of the formula (I) as hereinbefore defined either alone or in association with one or more pharmaceutically, veterinarally or agriculturally acceptable carriers or excipients.

An effective amount or a therapeutically effective amount of an endonuclease of the formula (I) is an amount effective to cause cleavage of target RNA and/or inactivation thereof (such as by the provision of an endonuclease of the formula (I) wherein the nucleotide sequences X and Y comprise a significant number of nucleotides, such that the endonuclease essentially binds irreversibly to the target) so as to ameliorate disease in a human, animal or plant subject. What constitutes an effective amount of an endonuclease will vary depending on the nature of the disease being treated, the mode of application of the endonuclease to the subject, health of the subject, weight of the subject, and other like factors, as are well known in the pharmaceutical art to be associated with pharmaceutical effectiveness (see The Pharmacological Basis of Therapeutics, 4th Edition, Lewis S. Goodman and Alfred Gilman, 1970, The Macmillan Company). What constitutes a therapeutically effective dose in any particular circumstance can be readily determined according to standard procedures known in the pharmaceutical art (see The Pharmacological Basis of Therapeutics, Supra). For example, titration experiments may be employed where the effect of an endonuclease in tissue culture is studied to determine toxicity and effectiveness. Thereafter, trials may be conducted on animals and thereafter human patients to determine toxicity, effectiveness, preferred mode of administration and the like. Such investigations are routine in the pharmaceutical art as mentioned above, and thus a therapeutically effective amount of an endonuclease may be readily determined without undue experimentation for medical or veterinary purposes.

A therapeutically effective amount of an endonuclease of the present invention would generally comprise from about 1 nM to about 1 mM concentration in a dosage form, such as a cream for topical application, a sterile injectable composition, or other composition for parenteral administration. In respect of topical formulations, it is generally preferred that between about 50 μM to about 500 μM endonuclease be employed. Endonucleases comprising nucleotide derivatives, which derivatives may involve chemically modified groups, such as phosphorothioate or methyl phosphonate derivatives may be active in nanomolar concentrations. Such concentrations may also be employed to avoid toxicity.

Therapeutic strategies involving treatment-of disease employing endoribonucleases of this invention are generally the same as those involved with antisense approaches, such as described in the anti-sense bibliography of Chrisley, L. A. (1991) Antisense Research and Development, 1: 65–113, which reference and all references therein are incorporated by reference. Particularly, concentrations of endonucleases utilised, methods and modes of administration, and formulations involved may be the same as those employed for antisense applications.

By way of example only, therapeutic compositions of this invention may be directed against Herpes Simplex virus types 1 and 2, psoriasis, cervical preneoplasia, papilloma disease, and bacterial and prokaryotic infection. Such treatments may, for example, involve topical application of endonucleases to the site of disease. For example, in the treatment of Herpes virus lesions, endonucleases may be formulated into a cream containing a concentration of 1 nM to 1 mM endonuclease. The cream may then be applied to the site of infection over a 1 to 14 day period in order to cause amelioration of symptoms of the infection. Prior to the final development of topical formulations for the treatment of Herpes virus infection, effectiveness and toxicity of the endonucleases and formulations involving them may, for example, be tested on an animal model, such as scarified mouse ear, to which virus particles, such as $2 \times 10^6$ plaque forming units are added. A titre of infectious virus particles in the ear after treatment can then be determined to investigate effectiveness of treatment, amount of nuclease required and like considerations.

Similar investigations in animal models prior to human trialing may also be conducted, for example, in respect of the treatment of psoriasis, papilloma disease, cervical preneoplasia, and in diseases such as HIV infection, bacterial or prokaryotic infection, viral infection and various neoplastic conditions, which neoplastic conditions involve a deleterious RNA species.

Pharmaceutically and veterinarally acceptable carriers and excipients are well known in the art, and include carriers such as water, saline, dextrose and various sugar solutions, fatty acids, liposomes, oils, skin penetrating agents, gel forming agents and the like, as described for example in Remington's Pharmaceutical Sciences, 17th Edition, Mack Publishing Co., Easton, Pa., Edited by Ostol et al., which is incorporated herein by reference.

Compositions for topical application are generally in the form of creams, where the endonucleases of this invention may be mixed with viscous components. In such embodiments, the endonucleases of this invention may be incorporated into liposomes or other barrier type preparations to shield the endonucleases from nuclease attack or other degradative agents (such as endonucleases and adverse environmental conditions such as UV light).

Compositions may be provided as unit dosages, such as capsules (for example gelatin capsules), tablets, suppositories and the like. Injectible compositions may be in the form of sterile solutions of endonuclease in saline, dextrose or other media. Compositions for oral administration may be in the form of suspensions, solutions, syrups, capsules, tablets and the like. Endonucleases may also be provided in the form of sustained release articles, impregnated bandages, patches and the like. Pharmaceutical compositions which may be used in this invention are described, for example, in Remington's Pharmaceutical Sciences, Supra.

The endonucleases of this invention may provided in a composition with one or more anti-viral, anti-fungal, anti-bacterial, anti-parasitic, anti-protazoan or anthelmentic agents, herbicides, pesticides or the like, for example as described in the Merck Index (1989) 11th Edition, Merck & Co. Inc.

Agriculturally acceptable carriers and excipients are well known in the art and include water; surfactants; detergents; particularly biodegradable detergents; talc; inorganic and/or organic nutrient solutions; mineral earths and clays; calcium carbonate; gypsum; calcium sulfate; fertilisers such as ammonium sulfate, ammonium phosphate and urea; and natural products of vegetable origin such as, for example, grain, meals and flours, bark meals; and the like.

The endonucleases of this invention have extensive application, stemming from the fact that virtually any RNA sequence may be cleaved by the endonucleases. The target nucleotide sequence GUC occurs, on a random basis, approximately once every 64 bases. The general endonuclease cleavage site X'UY', wherein X' and Y' are any nucleotide, occurs wherever. the base uracil is present in an RNA, and thus any target RNA should be cleavable, albeit at different efficiencies, using the endonucleases of this invention.

For in-vitro use, the endonucleases of this invention are generally reacted with a target RNA which contains one or more suitable cleavage sites. Optionally, the target RNA may be purified or substantially purified. The nucleotide sequences X and Y of the endonucleases of this invention are selected so as to specifically hybridise or form a double-stranded DNA duplex with a target RNA whereafter cleavage takes place. Accordingly, target RNA may be specifically cleaved in-vitro in the presence of other RNAs which themselves would not be cleaved by the endonucleases of this invention.

The endonucleases may be utilised in a manner similar to restriction endonucleases, that is for the specific cleavage of RNA to facilitate RNA manipulation. All that is required for such manipulations is that the target RNA to be cleaved contains a uracil base and thus a suitable cleavage site.

Endonucleases of this invention may be utilised in diagnostic procedures, such as the mapping or finger-printing of RNA. Specifically, the endonucleases of this invention would enable mapping of RNA and may be used to detect mutations in RNA sequence. Such procedures may be used in research and may also have forensic and other diagnostic applications.

RNA cleavage products in-vitro may be readily detected, for example, by visualisation on acrylamide or agarose gels where the amounts of RNA cleaved are sufficiently large for direct visualisation after separation and reaction with nucleotide visualisation agents, such as ethidium bromide. Alternatively, where the target RNA cleaved is present in small amounts, such as in a sample containing many RNAs, cleavage products may, for example, be detected by using radiolabelled probes of sequence complementary to the target sequence, or amplification techniques such as PCR (Sambrook et al., Supra).

A target RNA for cleavage in-vitro may be derived from any source, and may be of animal, viral, bacterial, plant, synthetic, or other origin. As RNA is common to all known living organisms, this invention may be utilised to cleave any RNA species having a suitable cleavage site as mentioned previously.

In-vitro cleavage of a target RNA is simply carried out by reacting the target RNA whether in purified, semi-purified or unpurified form, or a sample containing the target RNA, with an effective amount of an endonuclease under reaction conditions facilitating RNA cleavage. Suitable reaction conditions include a reaction temperature of about 4° C. to about 60° C. (preferably about 20 to 55° C.), pH from about 7.0 to about 9.0, and $Mg^{2+}$ from about 1 mM to about 100 mM (preferably 1 to 20 mM). The endonuclease may be present in an equimolar ratio to the substrate, or in excess thereof. As the endonucleases of this invention may act as enzymes, with each endonuclease cleaving multiple target sequences, the endonuclease may be provided in less than an equimolar ratio to target RNA.

According to an aspect of this invention, there is provided a method for the cleavage of the target nucleotide sequence in-vitro which comprises reacting said target nucleotide sequence or a sample containing said target nucleotide sequence with an endonuclease as described herein wherein nucleotide sequences X and Y of the nuclease are selected so as to be complementary to nucleotide sequences flanking a selected cleavage site of the target RNA, such that on hybridisation of the endonuclease to the target RNA, said target RNA is cleaved at the selected cleavage site.

In circumstances where the nucleotide sequences X and Y comprise a significant number of nucleotides, such as 30 or more nucleotides, the duplex formed on reaction of the endonuclease with its complementary target may not readily dissociate and hence such target RNAs may be inactivated not only by cleavage, but by blocking translation into a desired protein product, RNase H digestion, and/or prevention of interaction with other RNAs.

The endonucleases of this invention may be used for RNA cleavage in-vivo both in prokaryotic and eukaryotic cells.

The endonucleases of this invention may be utilised to cleave any RNA within a cell which contains the cleavage site X'UY' as described herein. Virtually all cellular RNAs would therefore be targetable utilising endonucleases of this invention.

Cleavage of target RNA within cells, such as bacterial cells, yeast cells, or animal cells, or the cleavage of a target RNA within the cells of an organism, such as a plant or animal, may result in phenotypic modifications or the treatment of disease or infection.

Phenotypic changes in plant cells or plants may include drought resistance, salinity resistance, resistance to fungal, viral or bacterial infection; modifications of growth characteristics; sterility; fruit production; flowering; senescence and the like. It is evident that once one or more RNAs involved in determining phenotype are identified, such RNAs may be inactivated by cleavage utilising the endonucleases of this invention and thus the phenotype of the plant or plant cell altered.

Phenotypic modifications within animals (including in some applications man) which may be effected by cleaving and thus inactivating target RNAs associated with phenotype would include growth characteristics of animals, fertility, skin/cosmetic modifications, reproductive characteristics, disease resistance and the like. Myriad applications arise for phenotypic modifications in animals, and plants as previously mentioned. Once one or more RNAs associated with a given phenotype are identified and their sequence determined, endonucleases may be targeted against such RNAs for their inactivation with consequential phenotypic modification.

Prokaryotic or eukaryotic cell cultures may be phenotypically modified by treatment with endonucleases of this invention. For example, bacterial cultures or yeast cultures involved in production of food components (such as cheese, bread and dairy products) and alcoholic beverage production may be treated so as to modify enzyme content, flavour production, cell growth rate, culture conditions and the like.

The endonucleases of this invention may also be used to treat disease or infection in humans, animals, plants, or prokaryotic or eukaryotic cells. The ability to treat disease or infection is based on the fact that the endonucleases of this invention are capable of cleaving any RNA which contains a suitable cleavage site, such as defined by the generic cleavage site X'UY', where X' and Y' represent any nucleotide (preferably wherein the cleavage site is GUC) as described previously. Most RNAs will contain one or more suitable cleavage sites.

The period of treatment would depend on the particular disease being treated and could be readily determined by a physician. Generally treatment would continue until the disease being treated was ameliorated.

Examples of human and animtal disease which may be treated with the endonucleases of this invention include Herpes Simplex Virus infection (such as targeting cleavage of early genes 4 and 5), psoriasis, cervical preneoplasia, papilloma disease, HIV infection (such as targeting the HIV-1 gag transcript and HIV-1 5'ltr splice site), bacterial and prokaryotic infection, viral infection and neoplastic conditions associated with the production of aberrant RNAs such as occurs in chronic myeloid leukemia. Diseases or infections which may be treated in plants with endonucleases of this invention include fungal infection, bacterial infections (such as Crown-Gall disease) and disease associated with plant viral infection.

Eukaryotic and prokaryotic cells in culture may, for example be protected from infection or disease associated with mycoplasma infection, phage infection, fungal infection and the like.

For the in-vivo applications of the endonucleases of this invention in humans, animals, plants, and eukaryotic and prokaryotic cells, such as in phenotypic modification and the treatment of disease, it is necessary to introduce the endonuclease into cells whereafter, cleavage of target RNAs takes place.

Methods for the introduction of RNA and DNA sequences into cells, and the expression of the same in prokaryotic and eukaryotic cells are well known in the art for example as discussed in Cotten, M. (1990) Tibtech 8: 174–178; and Friedman, T. (1989) Science 244: 1275–1280 (both of which references are incorporated herein by reference. The same widely known methods may be utilised in the present invention.

The endonucleases of this invention may be incorporated into cells by direct cellular uptake, where the endonucleases of this invention would cross the cell membrane or cell wall from the extracellular environment. Agents may be employed to enhance cellular uptake, such as liposomes or lipophilic vehicle, cell permeability agents, such as dimethylsulfoxide, and the like.

Endonucleases of this invention may be incorporated and expressed in cells as a part of a DNA or RNA transfer vector, or a combination thereof, for the maintenance, replication and transcription of the endonuclease sequences of this invention.

Transfer vectors expressing endoribonucleases of this invention may be capable of replication in a host cell for stable expression of endonuclease sequences. Alternatively, transfer vectors encoding endonuclease sequences of this invention may be incapable of replication in host cells, and thus may result in transient expression of endonuclease sequences. Methods for the production of DNA and RNA transfer vectors, such as plasmids and viral constructs are well known in the art and are described for example by Sambrook et al. (Supra).

Transfer vectors would generally comprise the nucleotide sequence encoding the endonuclease of this invention, operably linked to a promoter and other regulatory sequences required for expression and optionally replication in prokaryotic and/or eukaryotic cells. Suitable promoters and regulatory sequences for transfer vector maintenance and expression in plant, animal, bacterial, and other cell types are well known in the art and are described for example in Hogan, B. et al., (1986) Manipulating the Mouse Embryo, A Laboratory Manual, Cold Spring Harbor; and Science (1989) 244: 1275–137, which are incoporated herein by reference.

Transfer vectors or nucleic acid sequences encoding or comprising the endonucleases of this invention may be incorporated into host cells, such as plant or animal cells, by methods well known in the art (for example, as described by Cotten and Friedman (Supra), such as microinjection, electroporation, receptor-mediated endocytosis, transformation of competent cells such as protoplasts or bacterial cells treated with metal ions such as calcium chloride, cationic or other liposomes, viral or pseudovirus vectors, DEAE-Dextran, or by using projectiles to penetrate cell walls and thereby deliver the desired nucleic acid sequence.

In accordance with a still further aspect of this invention, there is provided a transfer vector which encodes a nucleotide sequences encoding an endonuclease as described herein.

Nucleotide sequences encoding the endonucleases of this invention may be integrated into the genome of a eukaryotic or prokaryotic host cell for subsequent expression (for example as described by Sambrook et al., Supra). Genomic integration may be facilitated by transfer vectors which integrate into the host genome. Such vectors may include nucleotide sequences, for example of viral or regulatory origin, which facilitate genomic integration. Methods for the insertion of nucleotide sequences into a host genome are described for example in Sambrook et al. and Hogan et al., Supra.

Genomically integrated nucleic acid sequences encoding the endonucleases of this invention generally comprise a promoter operably linked to the nucleotide sequence encoding the endonuclease of this invention, and capable of expressing said endonuclease in a eukaryotic (such as animal or plant cells) or prokaryotic (such as bacteria) host cells.

Endonucleases of this invention may be involved in gene therapy techniques, where, for example, cells from a human suffering from a disease, such as HIV are removed from a patient, treated with the endonuclease to inactivate the infectious agent, and then returned to the patient to repopulate a target site with resistant cells. In the case of HIV, nucleotide sequences encoding endonucleases of this invention capable of inactivating the HIV virus may be integrated into the genome of lymphocytes or be present in the cells a transfer vector capable of expressing endonucleases of this invention. Such cells would be resistant to HIV infection and the progeny thereof would also confer such resistance.

In accordance with an aspect of this invention, there is provided a method for the cleavage of a target nucleic acid sequence either in-vivo or in-vitro which comprises reacting a target nucleotide sequence with an effective amount of an endonuclease as described herein, said endonuclease being capable of effecting specific cleavage of said target at a site selected such as to cleave and inactivate the target nucleic acid sequence.

In accordance with another aspect of this invention, there is provided a method for the treatment of disease or infection in a human, animal, plant, or prokaryotic or eukaryotic cell, which is associated with the presence of a deleterious RNA, which method comprises treating said human, animal, plant, prokaryotic or eukaryotic cell with an effective amount of an endonuclease as described herein, either alone or in association with a pharmaceutically, veterinarally, or agriculturally acceptable carrier or excipient, which endonuclease is capable of cleaving and thus inactivating said deleterious RNA.

Recombinant DNA manipulations referred to above are well known in the art, and are described for example by Sambrook et al., Supra.

In another aspect of this invention, there is provided an animal or plant which comprises one or more cells which have been modified by, or contain, encode and/or express an endonuclease as herein defined.

The endonucleases of this invention may be produced by nucleotide synthetic techniques which are well known in the art, and described for example by Carruthers et al. (Methods in Enzymology (1987) 154: 287–313), Foehler et al. (Nucleic Acids Resarch (1986) 14: 5399–407) and Sprat et al. (Oligonucleotide Synthesis—A Practical Approach, IRL Press, Oxford (1984) M. J. Gait—Editor, pp. 83–115), all of which are incorporated herein by reference. Generally, such synthetic procedures involve the sequential coupling of activated and protected nucleotide bases to give a protected nucleotide chain, whereafter protecting groups may be removed by suitable treatment. Alternatively, the endonucleases in accordance with this invention may be produced by transcription of nucleotide sequences encoding said endonucleases in host-cells or in cell free systems utilizing enzymes such as T3, SP6 or T7 RNA-polymerase (Sambrook et al., Supra).

The catalytic region M of the endonucleases of this invention is of a reduced size compared with what may have been considered necessary from knowledge in the prior art. The absence of a conventional base-paired stem structure provided by an embodiment of the endonucleases of this invention may reduce steric interference of the endonuclease with its substrate or other nucleic acid structures and may also reduce the likelihood of non-favourable base pairing interactions particularly in the in-vivo context when the endonuclease may be in association with a large number of nucleic acids, in addition to the specific target which it is engineered to cleave.

The inclusion of deoxyribonucleotides in the endonuclease structure in certain embodiments of this invention may provide protection against ribonuclease degradation. Also, endonucleases comprised of RNA/DNA may not provide a substrate for unwinding/modifying enzymes which compromises some anti-sense applications. The reduced size of various embodiments of the endonuclease of this invention when compared with other endonucleases known in the art may serve to improve the economics of synthesis of the endonuclease and may also serve to improve the ease and efficiency of the introduction of the endonuclease into host cells.

Poly-endonucleases as described herein may be designed to have cleavage sequences within the flanking regions X and Y which link catalytic domains. Such poly-endonucleases may autocatalytically liberate multiple individual endonucleases in cells, thus increasing the local concentration of endonucleases.

The oligonucleotide backbone (that is, phosphodiester linkages) of compounds of the formula (I) may be modified in a variety of ways, for example, in the same manner as for DNA antisense oligonucleotides. Methylphosphonate, phosphorothioate and phosphoramidate linkages may be used to replace conventional phosphodiester linkages. Additionally, ribonucleotides may be substituted with modified nucleotides and/or bases, for example, 2'methoxyribonucleotides or [α]-anomers as described herein. These modifications may confer nuclease resistance and improve biological half-life and/or cellular uptake of endoribonucleases. Phosphorothioate linkages confer RNAse H sensitivity to the RNA component of RNA/DNA duplexes. Methylphosphonate linkages confer RNase H resistance to this same component.

Various embodiments to the present invention will now be described, by way of non-limiting example only, in the following examples.

EXAMPLE 1
Endonuclease Synthesis:

All endonucleotides were synthesized on either or both an Applied Biosystems 380 or 391 synthesizer using 2-cyanoethylphosphoramidite chemistry. DNA monomers and RNA monomers, protected at the 2' position with a t-butyldimethylsilyl group, were obtained from commercial suppliers. All oligonucleotides, with 5'-trityl groups removed, were worked up as follows: the oligonucleotide was cleaved from the column in 3:1 $NH_4OH$/ethanol, and heated overnight at 55° C. The solutions were evaporated to near dryness, taken up in $H_2O$/ethanol 3:1 and dried, and repeated. The amount of material was estimated at this stage by measuring the UV absorbance. The 2' group was deprotected by treatment overnight-with 1 M tetrabutylammonium fluoride in THF (10 µL per $OD_{260}$). The tetrabutylammonium ions were removed by passage twice through a Dowex 50x8-200 (trade mark) cation-exchange column in the $Na^+$form, the volume of the eluate was reduced with 2-butanol, and the oligonucleotide precipitated with sodium acetate and ethanol. The oligonucleotide was then purified by electrophoresis on a 10–20% (depending on length) acrylamide gel containing 7 M urea. The band of interest was visualised by UV shadowing or ethidium bromide staining, excised and soaked in water. The oligonucleotide solution was removed from the gel slices, concentrated with 2-butanol, washed with phenol/chloroform and ether. The oligonucleotide was then precipitated with sodium acetate and ethanol, washed with cold 80% ethanol, redissolved in 10 mM Tris-Cl, pH 8.0, 2 mM EDTA, quantified by UV spectroscopy, and frozen. Purity of the oligonucleotides was determined by labelling the 5' end with $^{32}P$ phosphate and running out in a denaturing gel. oligonucleotides were phosphorylated using standard conditions, except that several units of pancreatic ribonuclease inhibitor were added to the reaction mixture. Concentration of labelled material was determined by pooling all waste from the phosphorylation procedure, drying down, and running on a gel alongside a known fraction of the labelled oligonucleotide; and bands were excised and counted, and from this the amount of material lost in the phosphorylation procedure was known, and the concentration of the labelled oligonucleotide determined.

Reaction Conditions:

Typically reactions were conducted in 50 mM Tris.HCl, pH 8.0, 10 mM $MgCl_2$ at 37° C.; substrate concentration was 100 nM, and endonuclease concentration was 100 or 600 nM in all reactions. The reactions were conducted in a 30 µL volume over a range of 30 minutes to 4 hours. The molar ratio of endonuclease to substrate was 1:1 or 6:1. The endonuclease and substrate ($^{32}P$ labelled) were heated separately in reaction buffer to 70° C. for three minutes, then snap-cooled before mixing and subsequent incubation. Departures from the standard reaction conditions were taken as needed in experiments aimed at determining the temperature/activity profile, magnesium dependency, and pH dependency and turnover of the endonuclease mediated cleavage reaction. Samples were then analysed by electrophoresis in 15% acrylamide gels containing 7 M urea as a denaturant. The substrate and product of cleavage were visualised by autoradiography, and gel slices corresponding to their positions were excised and quantified by Cerenkov counting.

EXAMPLE 2
Growth Hormone RNA Targeted Endonucleases:

Base sequence, schematic representation and names of various endonucleases are set out below. Conserved ribonucleotides are depicted by bold type and thick lines. Other ribonucleotides are depicted by upper case letters and thin lines. Deoxyribonucleotides are depicted by lower case letters and wavy lines. The nomenclature for the endonucleases is as follows: R indicates a ribozyme containing helix II, M denotes an endonuclease not containing helix II, and MS denotes a endonuclease and substrate in the same molecule; the numbers and nucleotide designations indicates the bases in the connector, and the RNA or DNA refers to the nucleotides in the arms that form helices I and III with the substrate. Double helices I, II and III are as described by Forster and Symons (Cell (1987), 49: 211–220).

A further series of growth hormone RNA targeted endonucleases were synthesised based on the M4t,DNA construct and having different numbers and types of nucleotides in the connector. These are as follows:

M2t,DNA
M3t,DNA
M5t,DNA
Mttct,DNA
MttPDt,DNA

PD refers to 1,3-propanediol which was used in place of a nucleoside.

An endonuclease R4U,DNA was also synthesized. This endonuclease is the same as R4U,RNA depicted above, except that the RNA flanking sequences are replaced with DNA.

SUBSTRATES
Rat Growth Hormone 21 Mer's:

All of the above endonucleases were reacted with a ribonucleotide sequence corresponding to a portion of the rat growth hormone gene and having the sequence:

GHS1 5' A C C U G C G G G U C* A U G A A G U G U C 3'

A second substrate (GHS2) corresponding to GHS1 but where all nucleotides except C* were deoxyribonucleotides was also synthesized. Endonucleases M4U,RNA and M4U, DNA were reacted with this substrate.

Kruppel RNA:

The endonuclease M4t,DNA, Kr1079 (comprising 34 nucleotides and having flanking sequences of DNA designed to hybridise to the Kruppel target RNA) was tested against a short synthetic RNA substrate of 21 nucleotides and a RNA substrate of approximately 1.9 Kb, both containing the same cleavage site.

The Kr RNA transcript was prepared by inserting cDNA encoding the Kr transcript into a plasmid containing the T7RNA polymerase promoter. The Kr transcript was then transcribed with T7-polymerase.

The synthetic 21 mer was chemically synthesised and contained the same cleavage site as the longer RNA transcript. The 21 mer comprised the following (SEQ ID NO.:9)

A U U U G C G A G U C* C A C A C U G G A G where C* is a ribonucleotide.

In-vivo testing of activity of an anti-Kruppel endonuclease could be accomplished by microinjection of Drosophila embryos prior to the stage of syncytial blastoderm, in order to inactivate the 2.3 Kb RNA Kruppel transcript. Embryos (cuticlised embryos) can be assayed for abberant segmental pattern one to two days after egg laying.

Platelet Derived Growth Factor (PDGF):

The endonuclease Mttct,DNA, PDGF (a 30 mer, having flanking DNA sequences designed to hybridise to the PDGF target RNA) was reacted with a 666 base RNA transcript corresponding to exons 2 and 6 of the PDGF A gene from humans. A 666 base pair RNA transcript was transcribed in-vitro from a PDGF gene fragment using T3 polymerase.

RESULTS

A. All growth hormone RNA targetted endonucleases cleaved GHS1 with varying activities. In keeping with the endoribonuclease of Haseloff and Gerlach (Supra) and those of other investigators, no endonuclease cleaved 100% of product over the reaction period. Endonucleases M4T,DNA; M4U,DNA; M3T,DNA; M5T,DNA; and MTTCT,DNA; all cleaved between about 50–60% of substrate over the reaction period, this being about the same as the control R4U, RNA. Endonucleases containing less than four nucleotides in the connector (corresponding to the group P of the formula (II)) were somewhat less active in the test assay.

Experiments were conducted to examine the enzymatic turn over, temperature activity profile, magnesium dependency and pH dependence of representative minizyme M4T, DNA and a reference control, R4U,RNA, corresponding to the endoribonuclease of Haseloff and Gerlach (Supra). These experiments showed that both endonucleases behaved as enzymes exhibiting turn over, achieving cleavage of target substrate at pH 7.5, 37° C. and greater than or equal to 1 mM Mg2+.

It is clear from these results that functional endonucleases capable of cleaving target substrates may contain hybridising arms comprised of DNA or RNA, combinations thereof (corresponding to the groups X and Y of formula (I)); a connector comprised of a non-base paired RNA or DNA sequence, or a partly base paired RNA sequence and that the number and nature of nucleotides in the connecting sequence is not of importance.

The endonuclease MttPDt,DNA was active and shows that nucleotides may be replaced with chemical linking groups without loss of endonuclease activity. On the basis of this experiment, it is apparent that nucleotides in the connector sequence (corresponding to the group P of the formula (II)) may be replaced with linker sequences. B. The substrate GHS2 was cleaved by M4U,RNA but not M4U, DNA. It is presently unclear why the M4U,DNA endonuclease was not active against this substrate although this was obviously suggestive that the structure of a DNA-DNA duplex is sufficiently different from that of an RNA-RNA or an RNA-DNA duplex of the same sequence so as to possibly alter the structure of the active site and render the endonuclease inactive.

As the endonuclease M4U,RNA cuts a substrate made entirely of DNA, except for the central ribonucleotide, it is apparent that the only 2' hydroxyl on the substrate required for the cleavage reaction is on the nucleotide to be cleaved.

By altering the nucleotide composition of the flanking sequences of the endonuclease (corresponding to the groups X and Y of the formula (II)), any nucleotide substrate containing a suitable cleavage site may be cleaved. Optimisation of the flanking nucleotides as hereinbefore defined may be required to facilitate cleavage, as illustrated by the fact that M4U,RNA cleaves a substrate made entirely of DNA except for the central ribonucleotide having the base C, whereas the endonuclease M4U,DNA does not cleave this substrate.

Cleavage of the 1.9 Kb base Kruppel RNA and synthetic 21 mer RNA target hybrid was observed with the M4t,DNA, Kr1079 endonuclease.

Cleavage of the 1.9 Kb Kruppel RNA transcript indicates that large RNAs can be selectively cleaved at a desired cleavage site.

C. Similarly, an individual endonuclease effected efficient and specific cleavage of the long PDGF RNA transcript.

A synthetic RNA linked in cis to its target sequence, MS4U,RNA, was also active in effective specific cleavage at the predicted target sequence, at nanomolar concentrations with a rate independent of concentration. This provides evidence that this endonuclease does not form polymers or high molecular weight structures to effect cleavage, but rather that an individual discrete nuclease is capable of effecting catalytic cleavage of a target nucleotide sequence.

It is clear from the above examples that the endonucleases of this invention may be selectively used for the cleavage of any target RNA which contains an appropriate cleavage site (such as GUC) and whose nucleotide sequence is known. Accordingly, the endonucleases of this invention have wide application in the selective inactivation of target RNAs in-vivo and in-vitro and as such may be used for example for the treatment of disease in humans and animals, phenotypic alteration in animals and plants and other myriad applications.

We claim:

1. A compound comprising the structure:

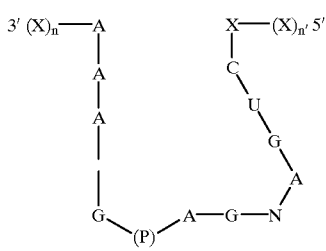

wherein each X represents a ribonucleotide or a deoxyribonucleotide which is the same or different and may be modified or substituted in its sugar, phosphate or base;

wherein each of A, C, U, and G represents a ribonucleotide;

wherein N may be any ribonucleotide;

wherein each one of $(X)_n$ and $(X)_{n'}$ represents an oligonucleotide in which n and n' are integers which define the number of nucleotides in the oligonucleotide, such oligonucleotide having a predetermined sequence sufficiently complementary to a predefined RNA target sequence to allow hybridization to the RNA target sequence;

wherein each solid line represents a covalent bond between the nucleotides located on either side thereof; and wherein P represents a linker which consists of a non-nucleotide connector and may contain one or more nucleotide which may be modified, wherein the non-nucleotide connector is selected from the group consisting of a polycyclic moiety, a polyphosphodiester, a polyamide, a polyglycol, a polypropanediol, and a combination of at least two of the foregoing, such that the length of the linker is equivalent to the length of 1–20 nucleotides.

2. The compound of claim 1, wherein each of X represents a ribonucleotide.

3. The compound of claim 1, wherein each X represents a deoxyribonucleotide.

4. The compound of claim 1, wherein the linker P is a polyphosphodiester, a polyglycol or a polypropanediol.

* * * * *

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 21 base pairs (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:1:

ACCUGCGGGU CAUGAAGUGU C                                               21

(2) INFORMATION FOR SEQ ID NO:2:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: Other nucleic acid
        (A) DESCRIPTION: (Mixed DNA/RNA oligomer
             see specification and figures for details)

(xi) SEQUENCE DESCRIPTION: SEQ ID NO:2:

GACACUUCAU CUGAUGAGUC CUUUUGGACG AAACCCGCAG GU                         42

(2) INFORMATION FOR SEQ ID NO:3:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: Other nucleic acid
        (A) DESCRIPTION: (Mixed DNA/RNA oligomer
             see specification and figures for details)

(xi) SEQUENCE DESCRIPTION: SEQ ID NO:3:

GACACUUCAU CUGAUGAUUU UGAAACCCGC AGGT                                 34

(2) INFORMATION FOR SEQ ID NO:4:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: Other nucleic acid
        (A) DESCRIPTION: (Mixed DNA/RNA oligomer
             see specification and figures for details)

(xi) SEQUENCE DESCRIPTION: SEQ ID NO:4:

GACACTTCAT CUGAUGAUUU UGAAACCCGC AGGT                                 34

(2) INFORMATION FOR SEQ ID NO:5:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: Other nucleic acid
        (A) DESCRIPTION: (Mixed DNA/RNA oligomer
             see specification and figures for details)

(xi) SEQUENCE DESCRIPTION: SEQ ID NO:5:

GACACTTCAT CUGAUGATTT TGAAACCCGC AGGT                                 34

(2) INFORMATION FOR SEQ ID NO:6:

(i) SEQUENCE CHARACTERISTICS:
    (A) LENGTH: 34 base pairs
    (B) TYPE: nucleic acid
    (C) STRANDEDNESS: single
    (D) TOPOLOGY: linear (ii) MOLECULE TYPE: RNA (genomic)

(xi) SEQUENCE DESCRIPTION: SEQ ID NO:6:

GACACTTCAT CUGAUGAAAA AGAAACCCGC AGGT                          34

(2) INFORMATION FOR SEQ ID NO:7:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:7:

GCGGGUCAUG AAGUUCGCUU CAUCUGAUGA UUUUGAAACC CG                 42

(2) INFORMATION FOR SEQ ID NO:8:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other nucleic acid
        (A) DESCRIPTION: (Mixed DNA/RNA oligomer
            see specification and figures for details)

(xi) SEQUENCE DESCRIPTION: SEQ ID NO:8:

ACCUGCGGGU CAUGAAGUGU C                                        21

(2) INFORMATION FOR SEQ ID NO:9:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:9:

AUUUGCGAGU CCACACUGGA G                                        21